United States Patent
Carney et al.

[11] 4,239,752
[45] Dec. 16, 1980

[54] O-DEMETHYLSELDOMYCIN FACTOR 5 DERIVATIVES

[75] Inventors: Ronald E. Carney, Gurnee; Robert L. Devault; James B. McAlpine, both of Libertyville; Arthur C. Sinclair, Lake Forest, all of Ill.

[73] Assignee: Abbott Laboratories, North Chicago, Ill.

[21] Appl. No.: 25,255

[22] Filed: Mar. 29, 1979

[51] Int. Cl.³ ................ A61K 31/71; C07H 15/22
[52] U.S. Cl. .................................. 424/180; 536/4; 536/17 R
[58] Field of Search ............... 536/17 R; 424/180

[56] References Cited

U.S. PATENT DOCUMENTS

| | | | |
|---|---|---|---|
| 3,939,043 | 2/1976 | Nara et al. | 536/17 |
| 4,002,608 | 1/1977 | Wright et al. | 536/17 |
| 4,045,610 | 8/1977 | Nara et al. | 536/17 |
| 4,124,756 | 11/1978 | Martin et al. | 536/17 |

Primary Examiner—Johnnie R. Brown
Attorney, Agent, or Firm—Robert L. Niblack; Gildo E. Fato; Joyce R. Niblack

[57] ABSTRACT

Derivatives of O-demethylseldomycin factor 5 represented by the following formula are provided:

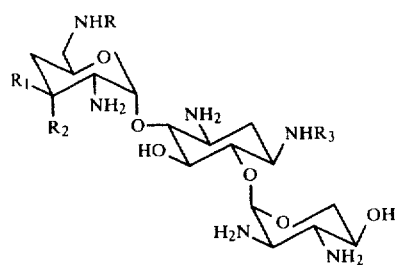

wherein: R is hydrogen or loweralkyl; $R_1$ and $R_2$ can be either hydrogen or hydroxy with the limitation that both $R_1$ and $R_2$ cannot be hydroxy; $R_3$ is selected from the group consisting of hydrogen, loweralkyl, aminoloweralkyl, diaminoloweralkyl, hydroxyloweralkyl, N-loweralkylaminoloweralkyl, aminohydroxyloweralkyl, N-loweralkylaminohydroxyloweralkyl, or

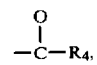

with the limitation that when $R_1$ is hydroxy, $R_3$ cannot be hydrogen when R is hydrogen; and $R_4$ is selected from the group consisting of loweralkyl, aminoloweralkyl, diaminoloweralkyl, hydroxyloweralkyl, N-loweralkylaminoloweralkyl, aminohydroxyloweralkyl and N-loweralkylaminohydroxyloweralkyl; and the pharmaceutically acceptable salts thereof. The compounds are potent anti-bacterial agents.

14 Claims, No Drawings

O-DEMETHYLSELDOMYCIN FACTOR 5 DERIVATIVES

BACKGROUND OF THE INVENTION

Seldomycin factor 5 is a broad spectrum antibacterial agent which is produced by the forementation of *Streptomyces hofunensis* as disclosed in U.S. Pat. No. 3,939,043. The antibiotic is represented by the following structure.

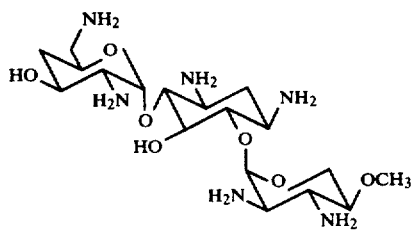

Seldomycin factor 5 is also known as Antibiotic XK-88-5. It is a highly active, broad-spectrum antibiotic effective against both Gram-positive and Gram-negative organisms such as *Staphylococcus aureus, Klebsiella pneumoniae, Escherchia coli* and Proteus, species.

Seldomycin factor 5 is only one of a number of antibiotics produced by the fermentation of *Streptomyces hofunensis*. The isolation and characteristics of seldomycin factor 5 is described in the above referred to U.S. Pat. No. 3,939,043 and the elucidation of its structure is described in the *Journal of Antibiotics* 30 pp 39-49 (1977).

Seldomycin factor 5 is an aminoglycoside antibiotic and the aminoglycoside antibiotics are a valuable therapeutic class of antibiotics which includes the kanamycins, streptomycins, gentamicins and fortimicins. While the naturally produced parent antibiotic are valuable, broad spectrum antibiotics, it has been found that chemical modification of the parent structures results in improved entities either by improving the intrinsic activity, improving the activity against resistant strains, or reducing the toxicity. Further, because of the development of aminoglycoside-resistant strains and inactivation of the parent antibiotics by R-mediated factors which can develop, the search for new entities continues which are either improved in one of the above-metioned ways or in providing reserve antibiotics which have useful activity.

A number of chemical modifications have been made in the seldomycin factor 5 structure. Those modifications have resulted in 3'-epi-seldomycin factor 5, 6'-N-alkylseldomycin factor 5 derivatives, 3'-deoxyseldomycin factor 5 and 1-N-acyl-seldomycin factor 5 derivatives among others. The above derivatives are the subject of pending United States patent applications and issued patents. 1-N-alkylseldomycin factor 5 derivatives are disclosed in U.S. Pat. No. 4,002,608.

The present invention provides a potent class of seldomycin factor 5 derivatives, O-demethylseldomycin factor 5 derivatives.

SUMMARY OF THE INVENTION

The present invention provides a new class of seldomycin factor 5 derivatives, O-demethylseldomycin factor 5 derivatives. The compounds of this invention are prepared by treating the seldomycin factor 5 derivative to be O-demethylated with lithium wire in the presence of ethylamine and recovering the O-demethylated compound by silica gel chromatogrphy.

DETAILED DESCRIPTION OF PREFERRED EMBODIMENTS

The present invention provides O-demethylseldomycin factor 5 derivatives which are represented by the formula:

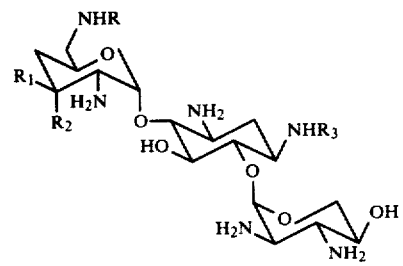

wherein: R is hydrogen or loweralkyl; $R_1$ and $R_2$ can be either hydrogen or hydroxy with the limitation that both $R_1$ and $R_2$ cannot be hydroxy; $R_3$ is selected from the group consisting of hydrogen, loweralkyl, aminoloweralkyl, diaminoloweralkyl, hydroxyloweralkyl, N-loweralkylaminoloweralkyl, amino-hydroxyloweralkyl, N-loweralkylaminohydroxyloweralkyl or

with the limitation that when $R_1$ is hydroxy, $R_3$ cannot be hydrogen when $R_1$ is hydrogen and $R_4$ is selected from the group consisting of loweralkyl, aminoloweralkyl, diamioloweralkyl, hydroxyloweralkyl, N-loweralkylaminoloweralkyl, aminohydroxyloweralkyl and N-loweralkylaminohydroxyloweralkyl, and the pharmaceutically acceptable salts thereof.

The term "loweralkyl", as used herein, refers to striaght or branched chain alkyl radicals containing from 1 to 6 carbon atoms inclusive and including, but not limited to methyl, ethyl, n-propyl, iso-propyl, n-butyl, sec-butyl, tert-butyl, n-pentyl, 1-methylbutyl, 2,2 dimethylbutyl, 2-methylpentyl, 2,2-dimethyl-n-propyl, n-hexyl and the like.

The term "pharmaceutically acceptable salts" refers to the non-toxic acid addition salts of the compounds of this invention which are generally prepared by reacting the free base with a suitable organic or inorganic acid, or can be prepared in situ by methods well known in the art. Such salts include the mino, di, tri, tetrapenta or hexa hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate and like salts.

The compounds of this invention are potent antibacterial agents which are effective against sensitive or susceptible strains of gram-negative and gram-positive bacilli such as *Bacillus subtilus, Staphylococcus aureas, Klebsiella pneumoniae, Proteus vulgaris, Proteus stuartii, Escherichia coli* and *Pseudomonas aeruginosa*. The antibiotics of this invention are administered parenteraly, i.e. intravenously, intramuscularly, intraperitoneally, or subcutaneously for systemic effect in daily dosages of from 2-10 mg/kg of body weight daily, and preferably from 4–6 mg/kg of body weight daily based on lean body weight as is good medical practice with the aminoglycoside antibiotics. It is further preferred to administer the compounds in divided dosages, i.e. three to four times daily.

The compounds can also be administered orally at the above doasage to sterilize the intestinal tract and can further be administered in suppository form.

The term "susceptible" or "sensitive" strains refers to strains of organisms which have demonstrated to be sensitive to a particular antibiotic in a standard in vitro sensitivity test and thus in vitro activity of an antibiotic against a specific strain of a specific bacillus has been established.

Generally speaking the compounds of this invention can be readily prepared by reacting the specific seldomycin factor 5 derivative to be O-demethylated with either lithium wire in the presence of ethylamine, or in the case of the acyl derivatives ($R_3=-COR_4$) with a boron trihalide such as boron tribromide, and recovering the O-demethylated derivative from the reaction mixture.

1-N-acylation can be accomplished by dissolving seldomycin factor 5 free base in a polar solvent and allowing the compound to complex with copper sulfate and then reacting the copper complex of seldomycin factor 5 with an active ester of benzylcarbonic acid which results in 3,2',6'-tri-N-carbobenzoxyseldomycin factor 5. Treatment of the latter with a suitable acylating agent in the presence of copper ion leads to 1-N-acyl-3,2',6'-tri-N-protected derivatives of seldomycin factor 5. These intermediates can be deprotected by methods well known in the art to yield the desired 1-N-acyl derivatives of seldomycin factor 5 which can be O-demethylated with a boron trihalide such as boron tribromide.

The 1-N-acyl-3,2',6'-protected intermediates may also be reduced to 1-N-alkyl-3,2',6'-tri-N-protected derivatives with, for example, treatment with diborane, and these intermediates in turn may be deprotected to yield the 1-N-alkyl derivatives of seldomycin factor 5 which can then be O-demethylated by treatment with lithium wire in the presence of ethylamine.

Suitable acylating agents are suitable active esters of carboxylic acids such as the acid anhydride, acid chloride or a carboxylic acid ester of N-hydroxy succinimide such as those disclosed in U.S. Pat. No. 4,091,032.

3'-Deoxyseldomycin factor 5 can be prepared by protecting the amine groups of seldomycin factor 5 with a suitable amine-protecting group such as substituted and unsubstituted acyl, alkoxycarbonyl and arylalkoxycarbonyl groups well known i the art and converting the per-N-protected seldomycin factor 5 to a thionoester at the hydroxyl group attached to the $C_3'$ carbon. Treatment of a per-N-protected intermediate with 1,1'-thiocarbonyldiimidazole in a suitable solvent such as tetrahydrofuran results in the 3'-imidazole-1-thiocarbonyl ester of the amine-protected seldomycin factor 5 with negligible ester formation at the hydroxyl attached to the $C_5$ carbon.

Treatment of the 3'-thienoester derivatives with tri-n-butylstannane is a suitable solvent such as dioxane results in replacement of the 3'-substituent with a hydrogen atom and results in the per-N-protected-3'-deoxyseldomycin factor 5 intermediate. Removal of the amine protecting groups by methods well known in the art results in 3'-deoxyseldomycin factor 5 which can then be subjected to appropriate modification and then O-demethylation or to O-demethylation.

3'-Epi-seldomycin factor 5 is obtained by converting the per-N-protected intermediate into a sulfonate ester at the hydroxyl group attached to the $C_3'$ carbon and heating the 3'-sulfonate ester in an inert solvent such as dimethyformamide and finally leaving the amine protecting groups with mild basis hydroysis followed by vigorous alkaline hydrolysis to yield 3'-epi-seldomycin factor 5 which can then be appropriately modified and O-demethylated.

6'-N-alkylation can be accomplished according to the methods set forth in the examples hereinbelow.

EXAMPLE 1

O-Demethylseldomycin factor 5

Seldomycin factor 5 (900 mg of free base prepared according to the method of U.S. Pat. No. 3,937,043) is suspended in freshly distilled ethylamine (100 ml) and the mixture is cooled to 0° C. and stirred vigorously as 4 cm of clean ⅛ inch diameter lithium wire is added. After one hour, the mixture is allowed to warm to gentle reflux and after a further 2½ hours, methanol is added to consume any unreacted lithium. Solvents are removed and the residue is chromatographed over a column (2.2 cm diameter × 60 cm) of silica gel. The column is eluted with a mixture of 1 volume of methylene chloride, 2 volumes of ethanol and 1 volume of concentrated ammonium hydroxide. Later fractions are combined and solvent is removed to yield O-demethylseldomycin factor 5 (585 mg).

EXAMPLE 2

Seldomycin factor 5-per-N-ethoxycarbamate

A mixture of 10.1 g of seldomycin factor 5 and 30 g of sodium carbonate are dissolved in 200 ml of distilled water and the solution is cooled in an ice bath. A mixture of 30 ml of ethylchloroformate and 50 ml of acetone is added dropwise and allowed to stand at room temperature for two hours. The precipitated product is removed by filtration, washed twice with 200 ml portions of water and dried in vacuo to yield 16.8 g of seldomycin factor 5 per-N-ethoxycarbamate.

Analysis Calcd. for $C_{36}H_{62}N_6O_{19}$: C, 48.97; H, 7.08; N, 9.52; Found: C, 48.98; H, 7.12; N. 9.48.

EXAMPLE 3

Seldomycin factor 5-per-N-ethoxycarbamate-3'-thioimidazolide

A solution of 15 g of seldomycin factor 5-per-N-ethoxycarbamate in 250 ml of anhydrous pyridine is diluted with 500 ml of tetrahydrofuran and treated with 6 g of 1,1'-thiocarbonyldiimidazole. The reaction mixture is heated under reflux for a further 16 hours and solvent is removed. Chromatography of the residue on a column of silica gel affods 16.4 g of seldomycin factor 5-per-N-ethoxycarbonate-3'-thioimidazolide.

Analysis Calcd. for $C_{40}H_{64}N_8O_{19}S$: C, 48.38; H, 6.50; N, 11.29; S, 3.22. Found: C, 48.34; H, 6.63; N, 11.11; S, 3.17.

EXAMPLE 4

3'-Deoxyseldomycin factor 5-per-N-ethoxycarbamate

A solution of 12.5 g of the compound of Example 3 in 750 ml of dioxane is added dropwise to a solution of 12.7 ml of tri-n-butylstannane in 1200 ml of dioxane. The mixture is heated under reflux in an atmosphere of nitrogen for two and one-half hours and then solvent is removed. Chromatography of the residue over a column of silica gel affords 9.8 g of the desired product.

Analysis Calcd. for $C_{36}H_{62}N_6O_{18}$: C, 49.88; H, 7.21; N, 9.69; Found: C, 49.60; H, 7.30; N, 9.45.

EXAMPLE 5

3'-Deoxyseldomycin factor 5-1N,3N-ureide

A solution of 4.7 g of the above prepared compound of Example 4 in 450 ml of 1.9 N methanolic sodium hydroxide is heated to pH 7 with 10 N sulfuric acid and solvent is removed. The residue is extracted with a mixture of chloroform-methanol-concentrated ammonium hydroxide[4:6:1(v/v/v)] and the extract is chromatographed over a column of silia gel to give 2.2 g of the desired intermediate.

EXAMPLE 6

3'-Deoxyseldomycin factor 5

4.7 g of 3'-deoxyseldomycin factor 5 per-N-ethoxycarbamate in 50 ml of methanol is added to 50 ml of 12 N aqueous potassium hydroxide solution and the mixture is heated in a sealed tube at 135° C. for 16 hours. The reaction mixture is adjusted to pH 7 with 10 N sulfuric acid and solvent is removed. The residue is extracted with a mixture of chloroform-methanol-concentrated ammonium hydroxide[4:6:1(v/v/v)]. The extract is chromatographed on a column of silica gel to give 2.3 g of 3'-deoxyseldomycin factor 5.

EXAMPLE 7

O-Demethyl-3'-deoxyseldomycin factor 5

3'-Deoxyseldomycin factor 5 (760 mg) is treated with lithium wire in ethylamine and the crude product chromatographed according to the method of Example 1 to yield 400 mg of O-demethyl-3'-deoxyseldomycin factor 5.

3'-Deoxyseldomycin factor 5 can also be prepared from the compound of Example 5 (2.42 g) according to the process of Example 6.

EXAMPLE 8

Seldomycin factor 5 per-N-ethoxycarbamate-3'-mesylate

A solution of 5 g of seldomycin factor 5 per-N-ethoxycarbamate in 120 ml of anhydrous pyridine is cooled in an ice bath and stirred as 1.3 ml of methanesulfonyl chloride are added. The mixture is allowed to warm to room temperature and to stand overnight. Solvent is removed and chromatography of the residue on a column of silica gel affords 4.0 g of the desired intermediate.

Analysis Calcd. for: $C_{37}H_{64}N_6O_{21}S$: C, 46.24; H, 6.71; N, 8.75; S, 3.34; Found: C, 45.85; H, 6.81; N, 8.56; S, 3.70.

EXAMPLE 9

3'-Epi-seldomycin factor 5-1,3,6',2'',3''-penta-N-ethoxycarbamate-3',3'-cyclic carbamate 3.5 Grams of the compound of Example 8 are dissolved in 100 ml of anhydrous dimethylformamide and the solution is heated at 90° C. overnight. Solvent is removed and chromatography of the residue on a column of silica gel affords 1.6 g of the desired intermediate.

Analysis Calcd. for: $C_{34}H_{56}N_6O_{18}$: C, 48.0; H, 6.75; N, 10.0; Found: C, 47.49; H, 6.73; N, 9.70.

EXAMPLE 10

3'-Epi-seldomycin factor 5

2.35 Grams of the compound of Example 9 in 50 ml of methanol are added to 50 ml of 12 N-aqueous potassium hydroxide solution and the mixture is heated in a sealed tube at 135° C. for 16 hours. The reaction mixture is adjusted to pH 7 with 10 N sulfuric acid and solvent is removed. The residue is extracted with a mixture of chloroform-methanol-concentrated ammonium hydroxide[1:2:1(v/v/v)]/. The extract is chromatographed on a column of silica gel to give 1.6 g of the desired product.

EXAMPLE 11

O-Demethyl-3'-epi-seldomycin fractor 5

3-Epi-seldomycin factor 5 (900 mg) is treated with lithium wire in ethylamine and the crude product chromatographed according to the method of Example 1.

EXAMPLE 12

3,2',6'-Tri-N-benzyloxycarbonylseldomycin factor 5

Seldomycin factor 5 free base (15 g) is dissolved in methanol (750 ml). Triethylamine (4.66 ml) is added, followed by copper sulfate pentahydrate (4.2 g) in methanol (50 ml). To a stirred solution of the seldomycin factor 5 copper complex is added the benzyloxycarbonyloxy ester of N-hydroxysuccinimide (30 g). After standing overnight, the mixture is taken to dryness under reduced pressure. Chromatography of the residue over silica gel using chloroform-methanol-concentrated ammonium hydroxide[50:50:5(v/v/v)] as the solvent system yields 9.0 g of the desired intermediate.

EXAMPLE 13

1-N Acetyl-3,2',6'-tri-N-benzyloxycarbonylseldomycin factor 5

To a solution of 3,2',6'-tri-N-benzyloxycarbonylseldomycin factor 5 (4.0 g) in methanol-tetrahydrofuran[3:2(v/v)] (200 ml) is added copper sulfate pentahydrate (567 mg) in methanol (40 ml). To a stirred solution of the resulting tri-N-benzyloxycarbonylseldomycin factor 5 copper complex, accetic anhydride (3.0 ml) is added. The mixture remains at room temperature overnight and is then evaporated to dryness under reduced pressure. Chromatography of the residue over silica gel using chloroform-methanol-concentrated ammonium hydroxide[90:10:1(v/v/v)] as the elution solvent affords 2.2 g of the desired intermediate.

EXAMPLE 14

1-N-Acetylseldomycin factor 5

1.26 Grams of the compound of Example 13 is dissolved in methanolic hydrogen chloride (150 ml) and hydrogenated overnight. The catalyst is removed by filtration and the filtrate taken to dryness in vacuo to yield 1.2 g of 1-N-acetylseldomycin factor 5 pentahydrochloride. Chromatography of the hydrochloride salt over Bio Rex AG1 X2(OH⁻ form) resin afforded 625 mg of 1-N-acetylseldomycin factor 5 free base.

EXAMPLE 15

1-N-Acetyl-O-demethylseldomycin factor 5

1-N-Acetylseldomycin factor (5) is dissolved in dry methylene chloride (25 ml) (distilled from calcium hydroxide and stored over Type A molecular sieve), cooled to 0° C. and treated with boron tribromide (10 ml). The mixture is stirred in a drying tube for 30 minutes at 0° C. and then for 16 hours at room temperature. Solvent and residual boron trihalide are removed in vacuo at 40° C. in a bath. Methanol (20 ml) is added to the reaction mixture and the mixture evaporated to a residue in vacuo at 40° C. and the step repeated twice.

The desired compound is isolated from the latter residue by silica gel chromatography using methylene chloride-methanol-concentrated ammonium hydroxide(2:3:1,v/v/v).

EXAMPLE 16

1-N-(4-Benzyloxycarbamido-2-hydroxybutyryl)-3,2',6'-tri-N-benzyloxcarbonylseldomycin factor 5

A stirred solution of 3,2',6'-tri-N-benzyloxycarbonylseldomycin factor 5 (512 mg) in methanol-chloroform(3:2,v/v) (25 ml) is added to a solution of copper sulfate pentahydrate (50 mg) in methanol (75 ml). To the resulting tri-N-benzyloxycarbonylseldomycin factor 5 copper complex is added 4-benzyloxycarbamido-2-hydroxybutyric acid ester of N-hydroxysuccinimide (1 g) in portions over a three hour period. The reaction mixture is allowed to remain at room temperature overnight and the solvent is then removed under reduced pressure. Chromatography of the residue over silica gal using chloroform-methanol-concentrated ammonium hydroxide[90:10:1(v/v/v)] as the elution solvent affords 180 mg of the desired material.

EXAMPLE 17

1-N-(4-Amino-2-L-hydroxybutyryl)seldomycin factor 5

The above intermediate (179 mg) is dissolved in methanolic hydrogen chloride (30 ml) and hydrogenated over 5% Pd/C (200 mg) at 3 atmospheres for six hours. The catalyst is removed by filtration and the filtrate taken to dryness in vacuo to yield 120 mg of product as the hydrochloride salt. Chromatography of this material over Bio Rex AG1 X2(OH⁻ form) resin affords 82 mg of 1-N-(4-amino-2-L-hydroxybutytyl)seldomycin factor 5 as the free base.

EXAMPLE 18

1-N-(4-Amino-2-L-hydroxybutyryl)-O-demethylseldomycin factor 5

One gram of the compound of Example 17 is O-demethylated according to the method of Example 15 using 10 ml of boron tribromide and the same reaction conditions to obtain the desired product.

EXAMPLE 19

O-Demethyl-1-N-ethylseldomycin factor 5

1-N-acetyl-3,2',6'-tri-N-benzyloxycarbonylseldomycin factor 5 (500 mg) is dissolved in tetrahydrofuran (200 ml) and diborane in tetrahydrofuran (5 ml) is added. After three hours at room temperature, excess diborane is consumed by the careful addition of water and the mixture taken to dryness in vacuo. Chromatography of the residue over silica gel in chloroform-methanol-concentrated ammonium hydroxide[75:25:2] affords 70 mg of 3,2',6'-tri-N-benzyloxycarbonyl-1-N-ethylseldomycin factor 5. Removal of the benzyloxycarbonyl-N-protecting groups by hydrogenolysis over 5% Pd/C in 43 ml of 0.2 N methanolic hydrogen chloride at 3 atmospheres and chromatography of the product over AG1 X2 (OH⁻ form) resin affords 35 mg of 1-N-ethylseldomycin factor 5 which is then O-demthylated using the method of Example 1.

EXAMPLE 20

1-N-(4-Amino-2-L-hydroxybutyl)-O-demethylseldomycin factor 5

The compound of Example 17 is reduced to 1-N-(4-amino-2-hydroxybutyl)seldomycin factor 5 according to the method of Example 19 and subsequently O-demethylated according to the method of Example 1.

The carbon magnetic resonance spectrum of 3'-deoxy-O-demethylseldomycin factor 5 is set forth in table I.

TABLE I

| Carbon Number | Assignment |
|---|---|
| 1 | 50.6 |
| 2 | 36.6 |
| 3 | 50.2 |
| 4 | 86.9 |
| 5 | 75.2 |
| 6 | 87.1 |
| 1' | 101.0 |
| 2' | 51.1 |
| 3' | 26.2 |
| 4' | 28.0 |
| 5' | 70.6 |
| 6' | 45.3 |
| 1" | 100.3 |
| 2" | 56.1 |
| 3" | 56.1 |
| 4" | 70.0 |
| 5" | 63.3 |

The above spectrum was determined in deuterium oxide with dioxane as internal reference taken as 67.4 ppm downfield from TMS. Assignments are made from analogy with other known seldomycin factor 5 derivatives and with consideration for the known effects of structural change on carbon magnetic resonance spectra. Interchange of assignments of resonances of similar chemical shift can be made without affecting the characterization of the compounds or the structural inferences of the spectra.

The in vitro antibiotic activity is determined by a two fold dilution test using Streptomycin Assay Agar with yeast extract (at pH 7.9). The inoculum of approximately $1 \times 10^5$ of the indicated test organism is delivered by a multiple inoculator. The minimum inhibitory concentrations for a representative compound, O-demethyl-3'-deoxyseldomycin factor 5 is set forth in Table II.

The minimum inhibitory concentrations are expressed in micrograms per milliliter.

TABLE II

| Organism | MIC(mcg/ml) |
|---|---|
| Bacillus subtilis U. of Ill. 10707 | 0.01 |
| Staphylococcus aureus ATCC 6538P | 0.02 |
| Klebsiella pneumoniae ATCC 10031 | 0.04 |
| Proteus vulgaris ATCC 6897 | 0.31 |
| Proteus stuartii ATCC 25825 | 2.5 |
| Eschericha coli ATCC 26 | 0.16 |
| Escherichia coli R3 | 2.5 |
| Escherichia coli R5 | 0.8 |
| Escherichia coli R16 | 0.4 |
| Escherichia coli R19 | 0.16 |

TABLE II-continued

| Organism | MIC(mcg/ml) |
| --- | --- |
| *Escherichia coli* 76-2 | 0.16 |
| *Escherichia coli* NR 79 | 0.16 |
| *Pseudomonas aeruginosa* BMH#1 | 0.63 |
| *Pseudomonas aeruginosa* KY-8512 | 1.25 |
| *Pseudomonas aeruginosa* PST | 720 |

The compounds of this invention are active as systemic antibiotics when administered by parenteral routes of administration as discussed hereinabove. They can be administered by the intramuscular, intravenous, intraperitoneal or subcutaneous routes of administration in daily dosages of from 2 to 10 mg/kg based on lean body weight. The compounds can also be administered orally to sterilize the intestinal tract and can also be applied topically or administered in suppository form.

Preparations of this invention for parenteral asministration include sterile aqueous or non-aqueous solutions, suspensions or emulsions. Examples of suitable nonaqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the composition, etc. They can be manufactured in the form of sterile solid compositions which can be dissolved in sterile water, or some other sterile injectable medium immediately before use.

Compositions for rectal administration are preferably suppositories which may contain, in addition to the active substance, excipients such as cocoa butter or a suppository wax.

Solid dosage forms for oral administration include tablets, pills, powders and granules. In such solid dosage forms, the active compound is admixed with at least one inert diluent such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings to ensure the antibiotic reaches the intestinal tract.

Liquid dosage forms for oral administration include pharmaceutically acceptable emulsions, solutions, suspensions, syrups and elixirs containing inert diluents commonly used in the art such as water. Besides such inert diluents, the liquid compositions can also include adjuvants such as wetting agents, emulsifying agents and suspending agents.

We claim:

1. A 3-O-demethylseldomycin factor 5 derivative represented by the formula

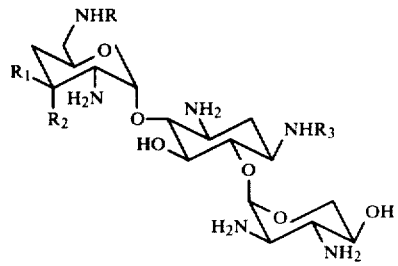

wherein: R is hydrogen or loweralkyl; $R_1$ and $R_2$ can be either hydrogen or hydroxy with the limitation that both $R_1$ and $R_2$ cannot be hydroxy; $R_3$ is selected from the group consisting of hydrogen, loweralkyl, aminoloweralkyl, diaminoloweralkyl, hydroxyloweralkyl, N-loweralkylaminoloweralkyl, aminohydroxyloweralkyl, N-loweralkylaminoloweralkyl or

and $R_4$ is selected from the group consisting of loweralkyl, aminoloweralkyl, diaminoloweralkyl, hydroxyloweralkyl, N-loweralkylaminoloweralkyl, aminohydroxyloweralkyl and N-loweralkylaminohydroxyloweralkyl, with the limitation that when $R_1$ is hydroxy, $R_3$ cannot be hydrogen when R is hydrogen, and the pharmaceutically acceptable salts thereof.

2. A compound of claim 1 wherein R is hydrogen.

3. A compound of claim 1 wherein R is loweralkyl.

4. A compound of claim 1 wherein R is hydrogen and R is

5. A compound of claim 1 wherein $R_3$ is loweralkyl.

6. A compound of claim 1 wherein $R_1$ is hydroxy.

7. A compound of claim 1 wherein $R_1$ is hydrogen.

8. A compound of claim 1: O-demethyl-3'-episeldomycin factor 5 or a pharmaceutically acceptable salt thereof.

9. A compound of claim 1: O-demethyl-3'-deoxyseldomycin factor 5 or a pharmaceutically acceptable salt thereof.

10. A compound of claim 1: 1-N-acetyl-O-demethyl seldomycin factor 5 or a pharmaceutically acceptable salt thereof.

11. A compound of claim 1: 1-N-ethyl-O-demethyl seldomycin factor 5 or a pharmaceutically acceptable salt thereof.

12. A compound of claim 1: 1-N-(4-amino-2-L-hydroxybutyryl)-O-demethyl seldomycin factor 5 or a pharmaceutically acceptable salt thereof.

13. A compound of claim 1: 1-N-(4-amino-L-2-hydroxybutyl)-O-demethyl seldomycin factor 5 or a pharmaceutically acceptable salt thereof.

14. A pharmaceutical composition comprising an antibacterially effective amount of a compound of claim 1 and a pharmaceutically acceptable carrier or diluent.

* * * * *